US00PP36689P2

(12) United States Plant Patent
Mackenzie

(10) Patent No.: US PP36,689 P2
(45) Date of Patent: May 20, 2025

(54) APPLE TREE NAMED 'MAC12'

(50) Latin Name: ***Malus domestica* Borkh**
Varietal Denomination: MAC12

(71) Applicant: Trajectory 752 Limited, Hastings (NZ)

(72) Inventor: Andrew John Mackenzie, Hastings (NZ)

(73) Assignee: Trajectory 762 Limited, Maraekakaho (NZ)

( * ) Notice: Subject to any disclaimer, the term of this patent is extended or adjusted under 35 U.S.C. 154(b) by 0 days.

(21) Appl. No.: 18/979,152

(22) Filed: Dec. 12, 2024

(51) Int. Cl.
*A01H 5/08* (2018.01)
*A01H 6/74* (2018.01)

(52) U.S. Cl.
USPC ..... Plt./161

(58) Field of Classification Search
USPC ..... Plt./161
See application file for complete search history.

*Primary Examiner* — Susan McCormick Ewoldt
(74) *Attorney, Agent, or Firm* — Michelle Bos Legal LLC

(57) ABSTRACT

A new and distinct apple tree named 'MAC12' having fruit notable for its attractive radiant red appearance, crisp and refreshing texture, excellent storage and long shelf life.

9 Drawing Sheets

Latin name: *Malus domestica* Borkh.
Variety denomination: 'MAC12'.

BACKGROUND AND SUMMARY OF THE INVENTION

The new apple tree 'MAC12' was created in the course of a planned breeding program carried out at Hawke's Bay, New Zealand. 'MAC12' originated in as a seedling from the open pollination of unreleased breeding selection 'PROP2' (seed parent, unpatented) by an unknown pollen parent. Initially given the breeder reference 'R5.2T12' and subsequently designated 'MAC12', the variety was selected in 2009 as a single plant from among a population of seedlings derived from the seed parent. Asexual propagation of the variety was first carried out in Hawkes Bay, New Zealand in 2017 by grafting onto 'MM106' rootstock (not patented). The variety has since been observed over a number of asexually propagated generations, and has been found to remain true to type. 'MAC12' is distinguished from its seed parent 'PROP2' by the shape of the fruit at harvest maturity, the form of the fruit stalk, and the overall tree vigor and predominant cropping habit.

| | 'PROP2' | 'MAC12' |
|---|---|---|
| Fruit shape | Obloid | Globose |
| Fruit stalk | Short, thick | Medium |
| Tree vigor | Low | Moderate |
| Predominant cropping habit | Spur bearing | Mix of spurs and shoots |

'MAC12' is distinguished from 'Scired' (not patented) and 'Cripps Pink' (U.S. Plant Pat. No. 7,880) by the following characteristics:

| | 'Scired' | 'Cripps Pink' | 'MAC12' |
|---|---|---|---|
| Fruit size | Medium | Large | Large |
| Maturity | Mid-season | Late | Late |

-continued

| | 'Scired' | 'Cripps Pink' | 'MAC12' |
|---|---|---|---|
| Fruit over color | Red | Pinkish/red | Vivid red |
| Fruit pattern of over color | Block | Blush | Block |
| Tree habit | Spreading | Upright | Spreading |
| Skin | Smooth | Bumpy, greasy | Smooth, dry |
| Russet sensitivity | Medium | Absent | Low |

BRIEF DESCRIPTION OF THE PHOTOGRAPHS

The accompanying photographs show typical specimens of 'MAC12' trees, foliage, and fruit, depicted in colors as true as reasonably possible. The photographs were obtained during the 2024 growing season at Hawke's Bay, New Zealand.

DETAILED BOTANICAL DESCRIPTION OF THE VARIETY

Figure 1:
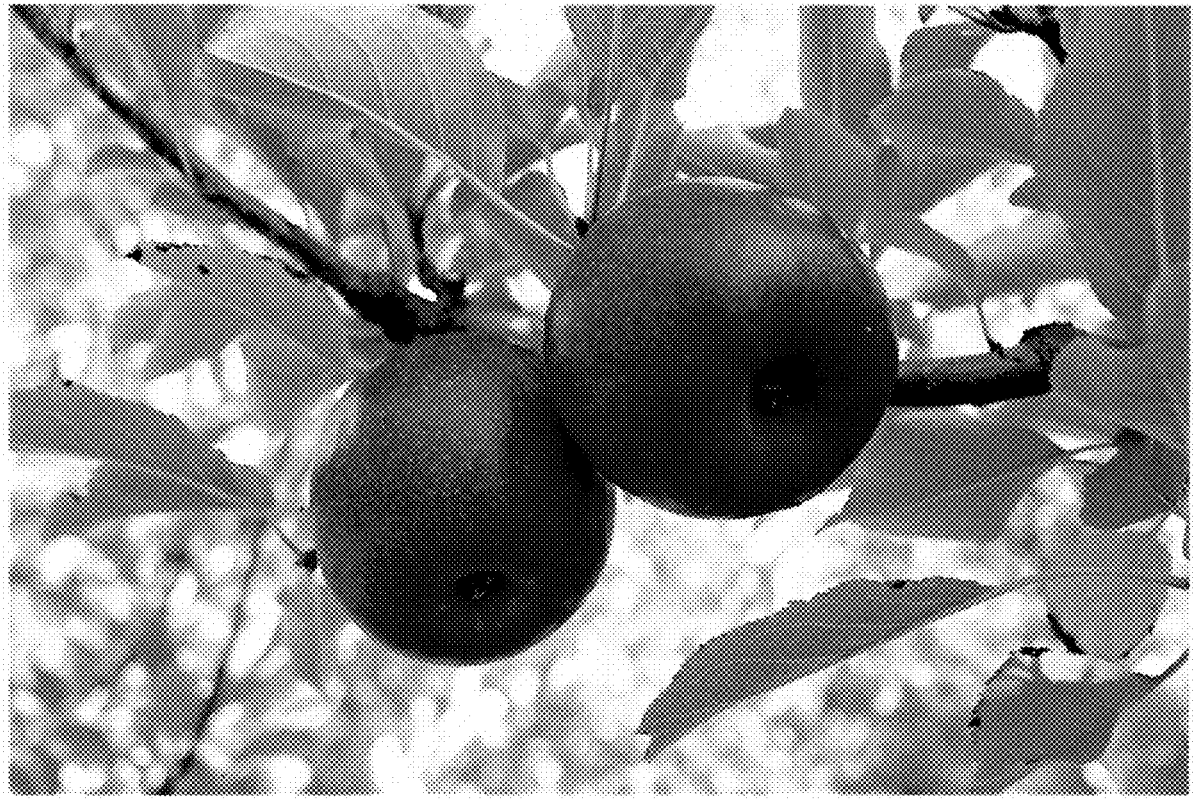
FIG. 1 shows a typical fruit of the apple variety 'MAC12' photographed in situ on the tree.
Figure 2:
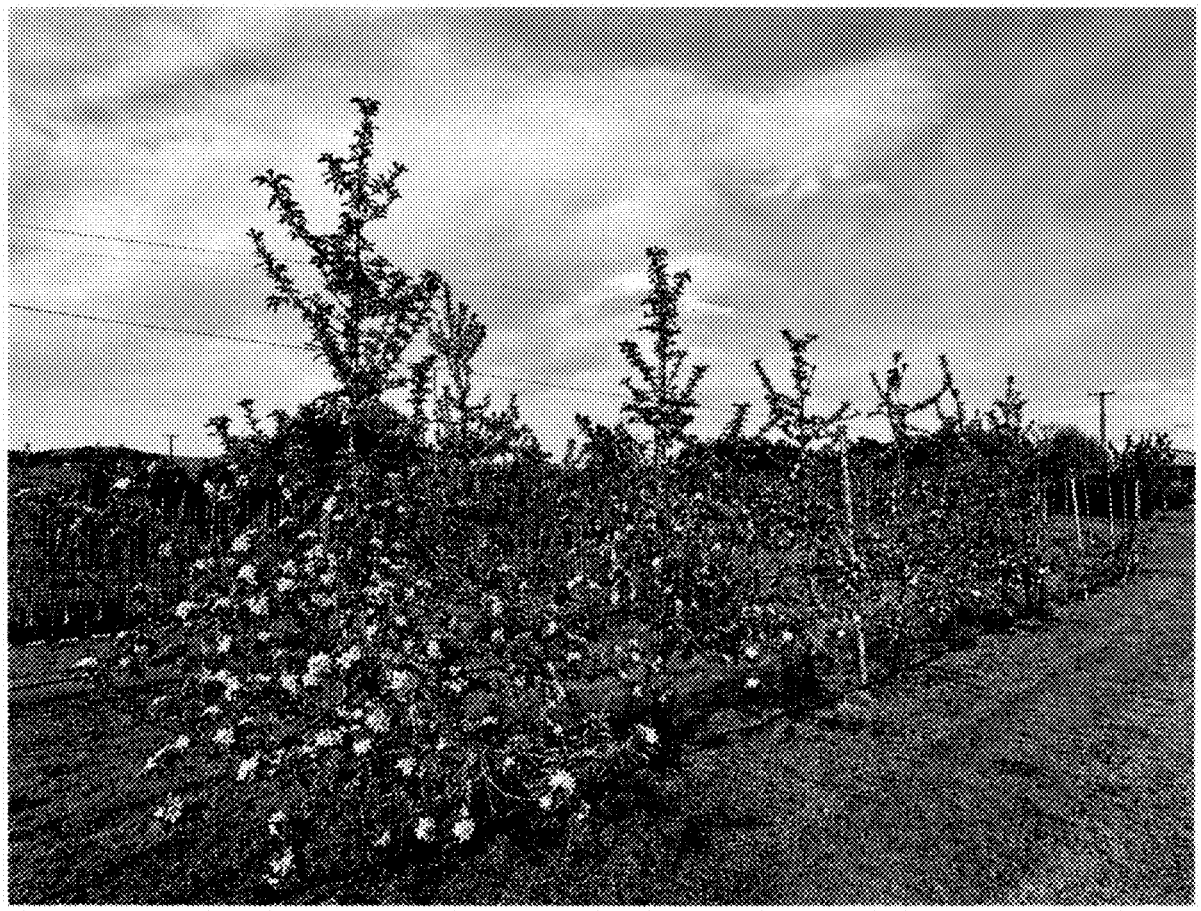
FIG. 2 shows four-year-old trees on M9 rootstock.
Figure 3:
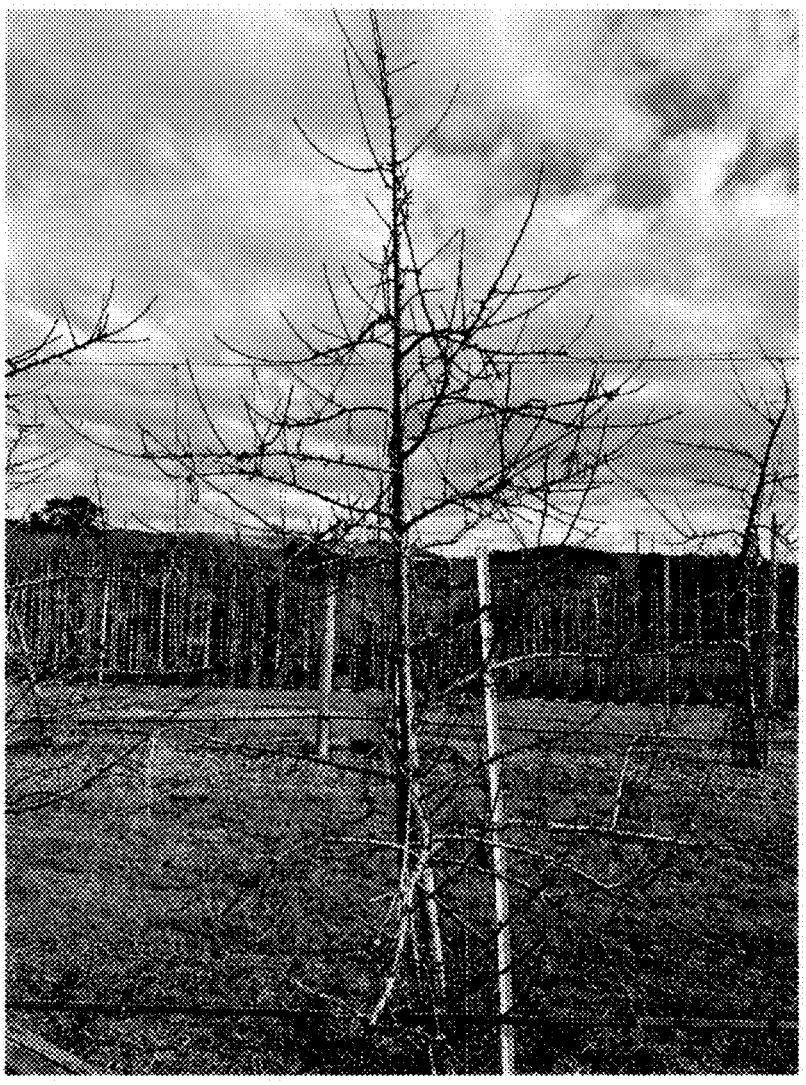
FIG. 3 shows a four-year-old tree showing typical branching development.
Figure 4:
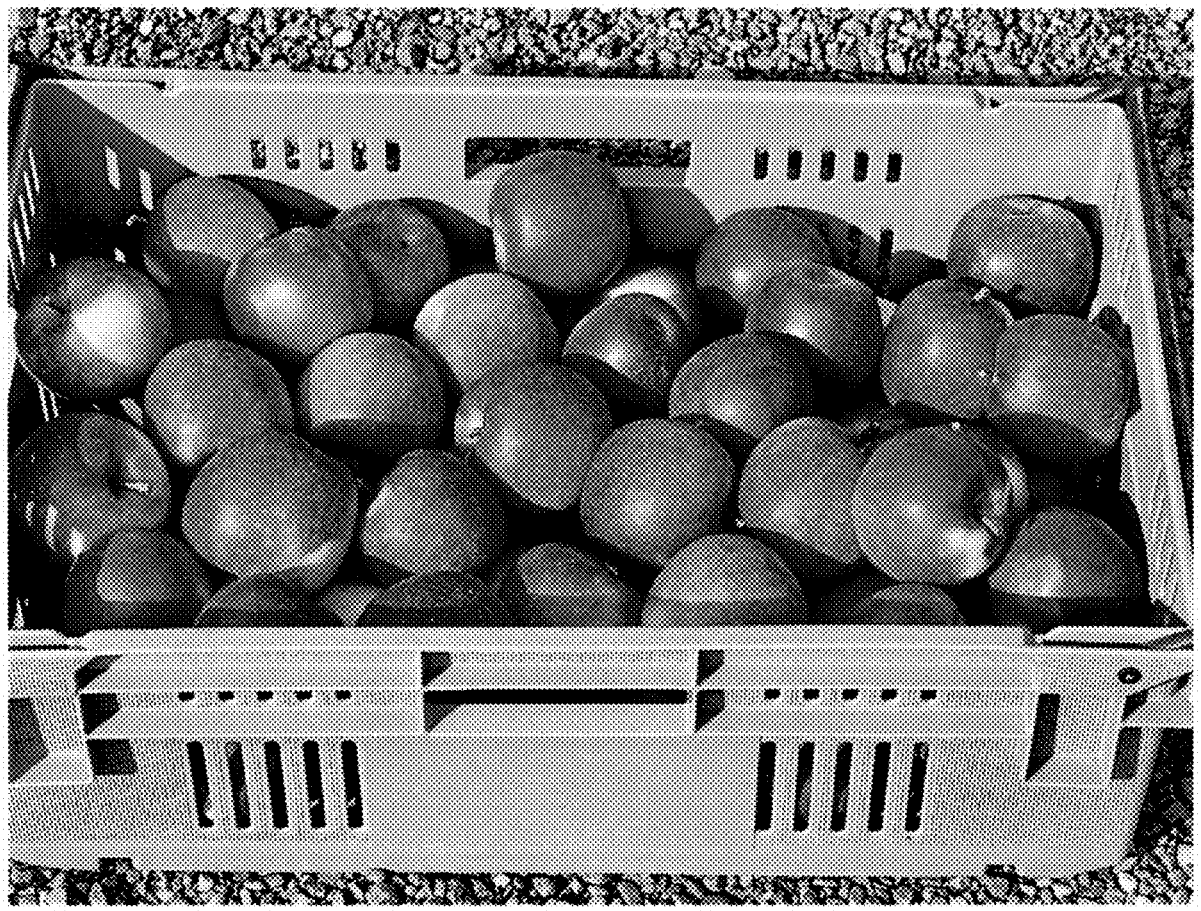
FIG. 4 shows typical fruit from a third-generation tree at harvest maturity 13 Apr. 2024.
Figure 5:
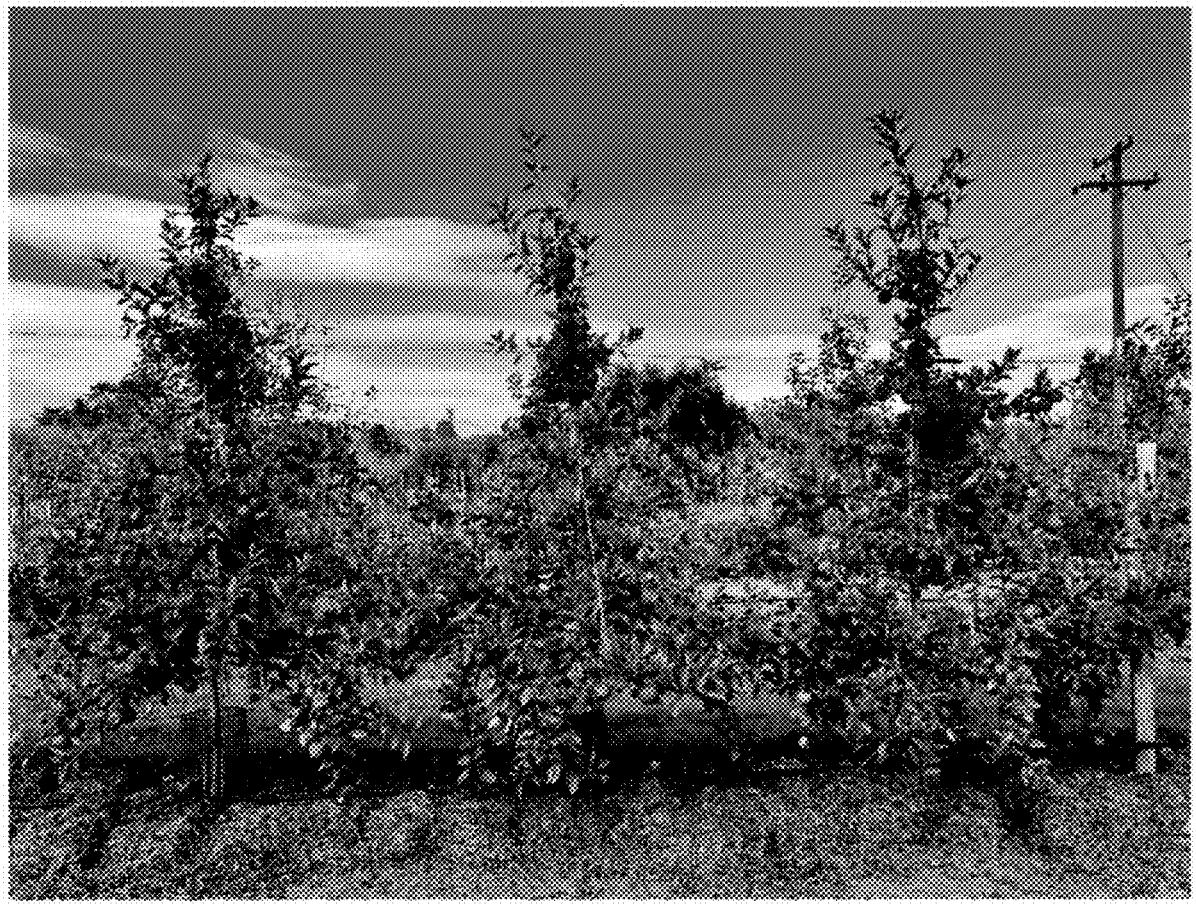
FIG. 5 shows fruit on a third-generation tree at harvest maturity 13 Apr. 2024.
Figure 6:
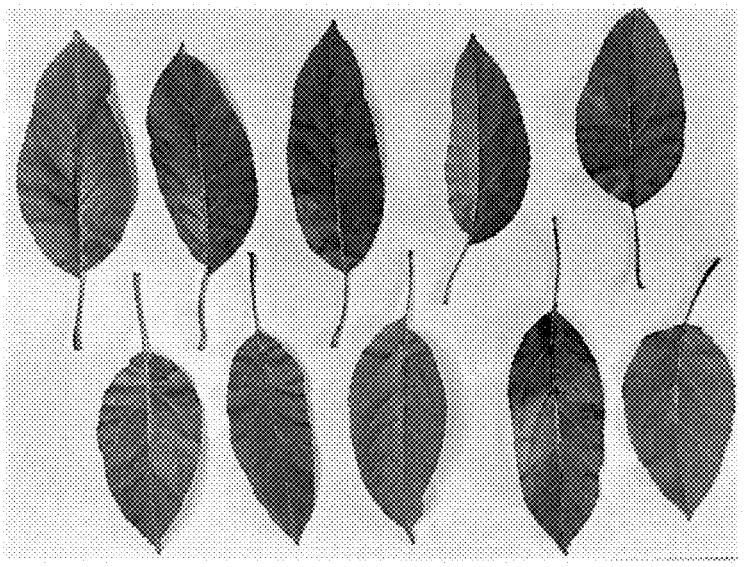
FIG. 6 shows the upper surface of mature leaves taken from a four-year-old tree.
Figure 7:
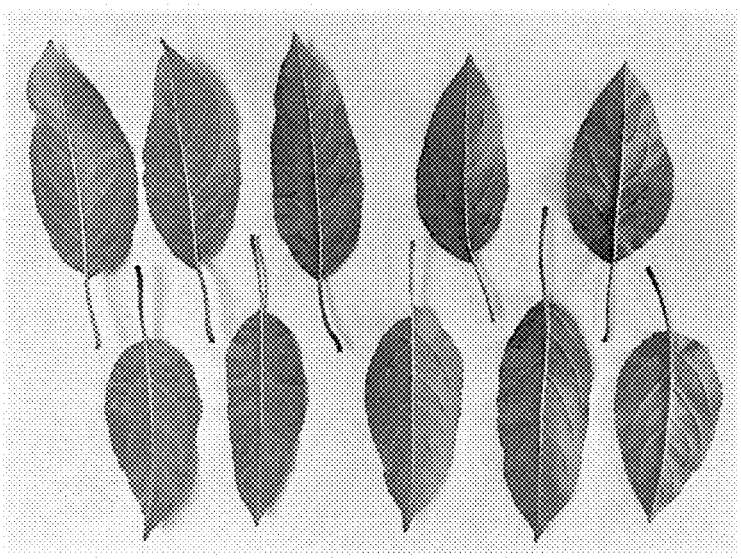
FIG. 7 shows the lower surface of mature leaves taken from a four-year-old tree.
Figure 8:
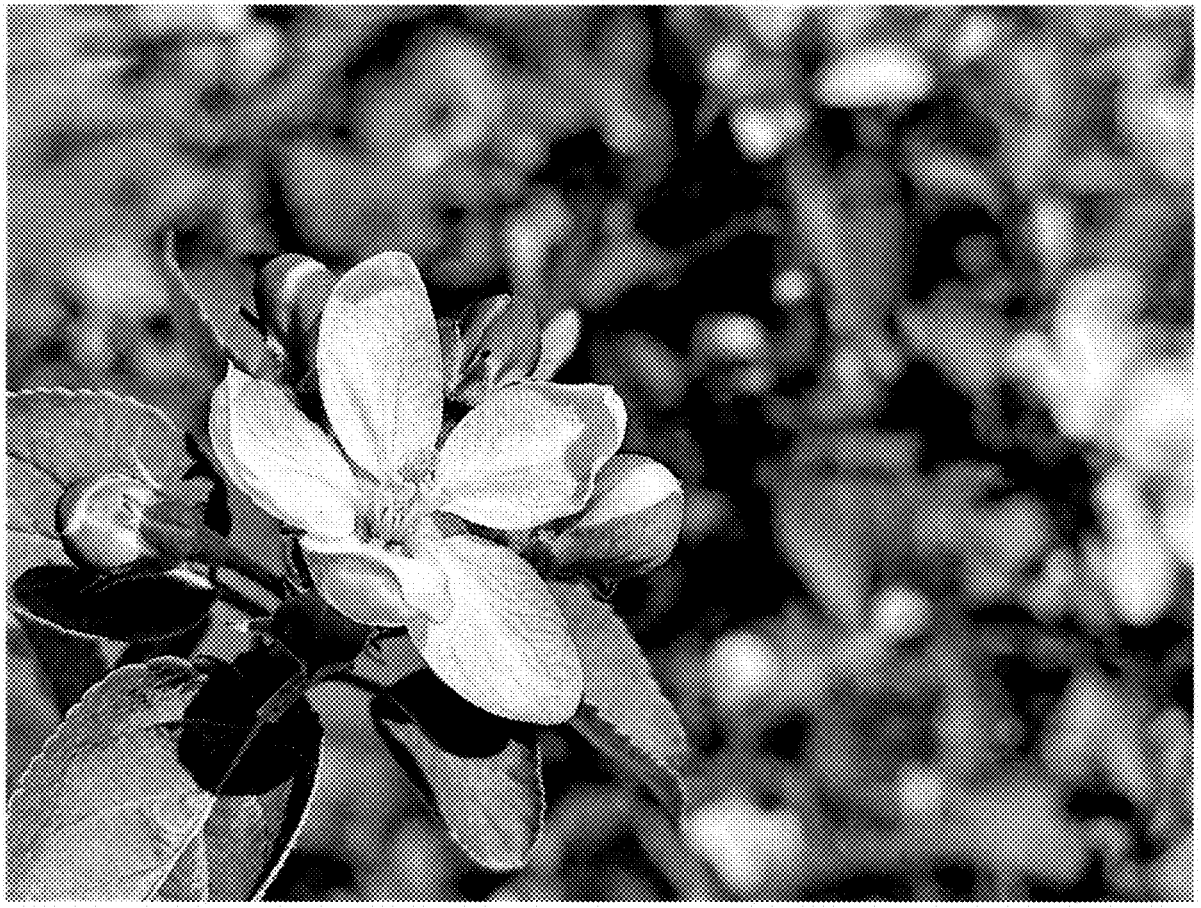
FIG. 8 shows typical flowers of 'MAC12' from a four-year-old tree.
Figure 9:
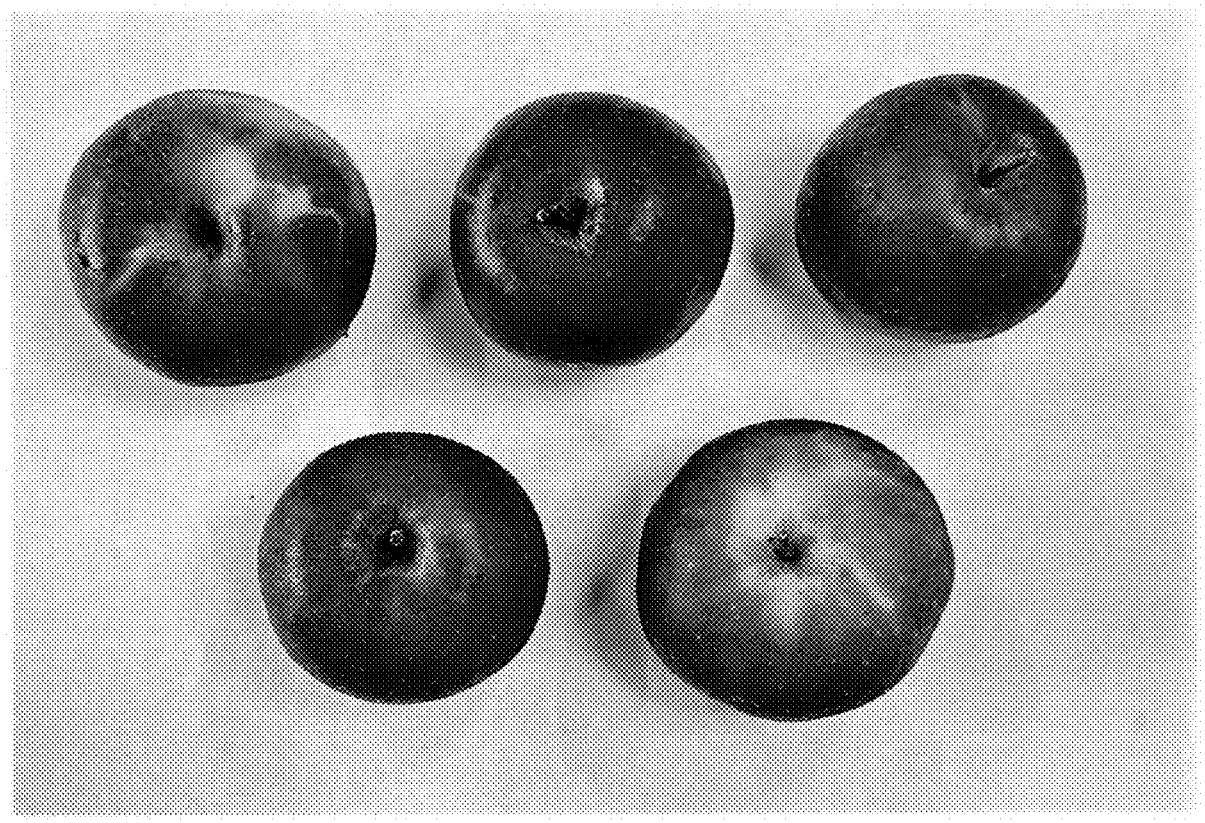
FIG. 9 shows fruit of 'MAC12' after 7 months storage.
Figure 10:
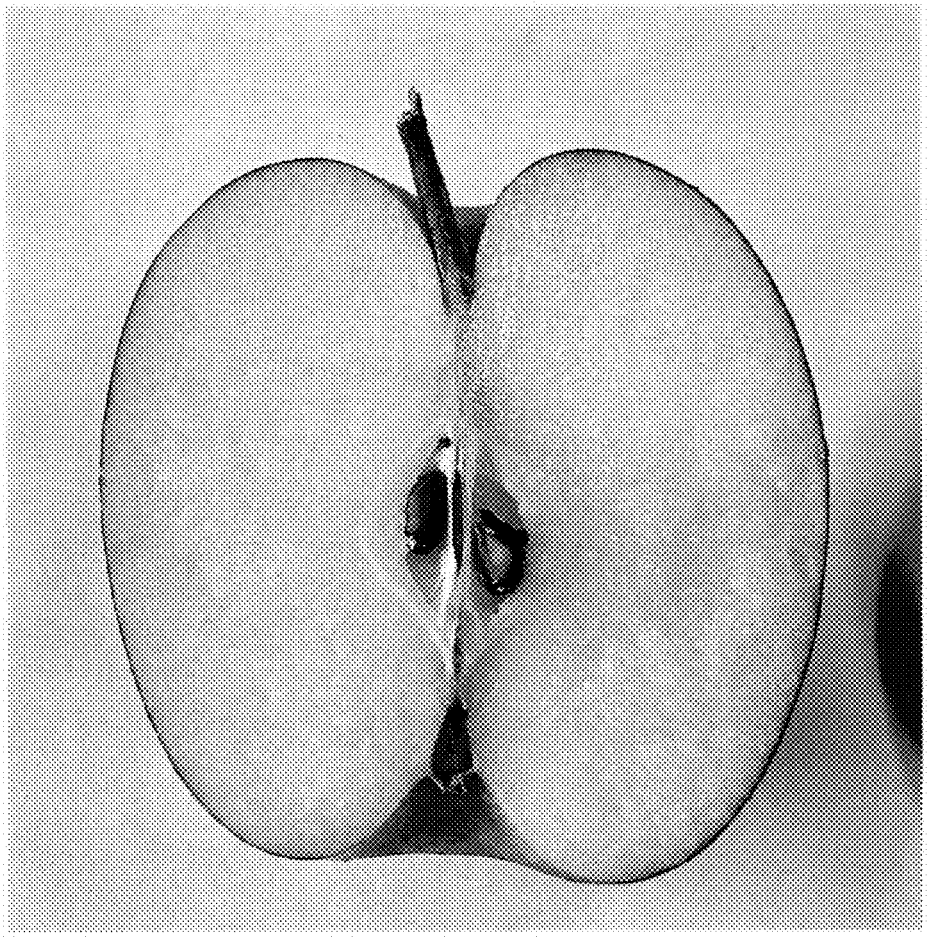
FIG. 10 shows cut fruit of 'MAC12' after 7 months storage.

The following detailed botanical description is based on observations of three-year-old trees on 'M9' rootstock (not patented) made during the 2024 growing season at Hawke's Bay, New Zealand. All colors are described according to The Royal Horticultural Society Colour Chart (Sixth edition 2015; 2019 reprint). It should be understood that the characteristics described will vary somewhat depending upon cultural practices, climatic conditions, and can vary with location and season. Quantified measurements are expressed as an average of measurements taken from a number of individual plants of the new variety. The measurements of any individual plant, or any group of plants, of the new variety may vary from the stated average.

Tree:

*Type*.—Ramified.
*Vigor*.—Moderate; typical volume of annual extension growth is similar to 'Tenroy Gala' (U.S. Plant Pat. No. 4,121), greater than maternal parent 'Prop2'.
*Habit*.—Spreading.
*Bearing*.—On shoots and spurs.
*Height*.—380 cm.
*Diameter*.—350 cm.
*Trunk circumference at* 30 *cm above the graft union*.—17.2 cm.
*Bark texture*.—Smooth to slightly rough.
*Bark coloration*.—Dark Greyish Yellow 199D.
*Lenticel shape*.—Elongated, raised.
*Lenticel length*.—2 mm to 3 mm.
*Lenticel width*.—0.5 mm to 1 mm.
*Lenticel color*.—Light Yellow Green 150D.
*Lenticel density*.—27 per 5 $cm^2$.

Branch:

*Length*.—163 cm.
*Circumference at* 10 *cm from the trunk*.—8.2 cm.
*Crotch angle*.—75° to 80°.
*Color of upper and lower surfaces*.—Light Yellowish Brown 199C.
*Lenticel shape*.—Elongated, linear, slightly raised.
*Lenticel length*.—2 mm to 3 mm.
*Lenticel width*.—0.5 mm to 1 mm.
*Lenticel color*.—Light Yellow Green 150D.
*Lenticel density*.—17 per 2.5 $cm^2$.

One-year-old shoot:

*Length*.—36 cm.
*Diameter at base*.—0.6 cm.
*Internode length*.—2.4 cm.
*Color*.—Moderate Orange 166D.
*Lenticel shape*.—Ellipsoid, linear, smooth.
*Lenticel length*.—0.5 mm to 1 mm.
*Lenticel width*.—0.5 mm.
*Lenticel color*.—Light Yellow Green 150D.
*Lenticel density*.—11 per $cm^2$.

Flower buds (described at dormancy, prior to spring bud movement):

*Quantity per spur*.—1 to 2.
*Shape*.—Conical.
*Apex shape*.—Pointed.
*Length*.—0.8 cm.
*Diameter*.—0.4 cm.
*Overcolor*.—Yellowish White 196D.

Flowers:

*Color at balloon stage*.—Moderate Purplish Pink 65A.
*Diameter of fully open flower*.—4 cm.
*Depth of fully open flower*.—1 cm.
*Arrangement of petals*.—Intermediate between free and overlapping.
*Relative position of petal margin*.—Not touching.
*Number per cluster*.—5.
*Date of first bloom*.—Around September 25.
*Date of full bloom*.—Around October 3.
*Pollination requirement*.—Cross-pollination recommended to ensure heavy crops of large fruit; 'Tenroy Gala' flowers at the same time and is an effective pollinizer.

Petals:

*Number per flower*.—5.
*Petal shape*.—Oval.
*Apex shape*.—Round.
*Base shape*.—Oblique.
*Margin*.—Smooth.
*Texture*.—Slightly marbled.
*Length*.—2 cm.
*Width*.—1 cm.
*Color of upper surface*.—Yellowish White NN155D with Deep Purplish Pink N66D irregularly distributed, associated with the veins, showing through from the underside.
*Color of lower surface*.—Yellowish White NN155D with Deep Purplish Pink N66D irregularly distributed, associated with the veins.

Pistils:

*Position of stigmas relative to anthers*.—Above.
*Length on opened flower*.—1 cm.
*Color*.—Light Yellow Green 145C.

Stigma:

*Quantity*.—5.
*Diameter*.—0.05 cm to 0.1 cm.
*Color*.—Light Yellow Green 145C.

Style:

*Length*.—1.1 cm.
*Color*.—Light Yellow Green 145C.

Ovary:

*Length*.—0.4 cm.
*Width at widest point*.—0.3 cm.
*Color*.—Moderate Yellow Green 138C.

Stamens:

*Quantity*.—20.
*Size, including anther and filament*.—0.8 cm.
*Color of pollen*.—Pale Greenish Yellow 9D.
*Abundance of pollen*.—Abundant.

Pedicel:

*Length*.—1.6 cm.
*Width*.—0.1 cm.
*Color*.—Strong Yellow Green 144A.

Sepals:

*Quantity*.—5.
*Color*.—Strong Yellow Green 144A.
*Length*.—0.8 cm.
*Width*.—0.3 cm.
*Shape*.—Slightly narrow cordate.
*Apex shape*.—Blunt.
*Margin*.—Serrate.

Leaves:

*Length*.—11.5 cm.
*Width*.—5.3 cm.
*Length to width ratio*.—2:1.
*Leaf shape*.—Ovate.
*Apex*.—Acuminate.
*Base shape*.—Acute.
*Blade margin*.—Serrate.
*Venation*.—Pinnate.

*Color of upper surface*.—Ranging Moderate Green N138A to Dark Yellowish Green 139A.
*Color of lower surface*.—Moderate Yellowish Green N138B.
*Texture of upper surface*.—Smooth.
*Pubescence on underside*.—Faintly pubescent.
*Stipules*.—Largely absent, insignificant where present.
*Leaf bud arrangement*.—Alternate.
*Attitude in relation to shoot*.—65°.

Petiole:
*Color*.—Strong Yellow Green 145A.
*Length*.—3.4 cm.
*Diameter*.—0.1 cm.

Fruit:
*Quantity per cluster*.—2 to 5; average 3.
*Height*.—6.8 cm.
*Maximum diameter*.—7.7 cm.
*Weight*.—200 g.
*Shape*.—Globose.
*Position of widest point*.—Equator.
*Ribbing*.—Absent.
*Crowning at calyx end*.—Present but not pronounced.
*Depth of eye basin*.—0.7 cm.
*Width of eye basin*.—3.1 cm.
*Size of eye*.—6 mm.
*Aperture of eye*.—Closed.
*Russet around eye*.—Absent.
*Length of stalk*.—1.7 cm.
*Thickness of stalk*.—0.2 cm.
*Stalk color*.—Brownish Orange N170A.
*Width of stalk cavity*.—2.8 cm.
*Depth of stalk cavity*.—0.9 cm.
*Russet around stalk cavity*.—Present.
*Aperture of locules*.—Moderately open.
*Sinus*.—Closed.
*Size of lenticels*.—Large.
*Density of lenticels*.—7 per $cm^2$.
*Background color of skin*.—Greenish Yellow 8C.
*Over color of skin*.—Strong Red 46A.
*Relative area of over color*.—60% to 80%.
*Pattern of over color*.—Solid flush.
*Intensity of over color*.—Medium.
*Russet on cheeks*.—None.
*Bloom of skin*.—Slight.
*Greasiness of skin*.—Absent.
*Skin thickness*.—0.2 mm.
*Flesh firmness*.—Firm; 10.0 kg at harvest; 8.7 kg after storage.
*Flesh texture*.—Crisp, crunchy and juicy; melting-style pomace.
*Juiciness*.—Moderate.
*Brix*.—14% at harvest; 17% after storage.
*Flesh color*.—Pale Yellow 12D.
*Starch pattern index* (*SPI*).—4.3.

Seeds:
*Quantity per fruit*.—5.
*Color*.—Moderate Reddish Brown 175A.
*Length*.—0.9 cm.
*Diameter*.—0.5 cm.
*Shape*.—Pear-shaped with pointed end.
*Length*.—0.9 cm.
*Width*.—0.5 cm.
*Thickness*.—0.3 cm.

Harvest maturity: Late-season; 13 Apr. 2024 in Hawke's Bay, New Zealand.
Number of picks: Typically 2.
*Yield per tree* (*unthinned*).—56.3 kg.
Disease and pest resistance and susceptibility: Low susceptibility to powdery mildew has been observed.
Drought tolerance: Average for domestic apple.
Tree winter hardiness: Average for domestic apple.
Shipping and storage quality: Excellent; 4 to 6 months in conventional cool storage at 0.5° C.
Use: Fresh Market, dessert.

The invention claimed is:

1. A new and distinct apple tree variety named 'MAC12', substantially as shown and described herein.

* * * * *